United States Patent
Du et al.

(10) Patent No.: US 8,034,983 B2
(45) Date of Patent: Oct. 11, 2011

(54) PROCESS FOR THE PREPARATION OF XANTHOPHYLL CRYSTALS

(75) Inventors: Jian Du, Beijing (CN); Chenghai Zhao, Beijing (CN)

(73) Assignee: Multi-Tech Specialty Chemicals, Co., Ltd., Tianjin (CN)

( * ) Notice: Subject to any disclaimer, the term of this patent is extended or adjusted under 35 U.S.C. 154(b) by 0 days.

(21) Appl. No.: 12/602,706

(22) PCT Filed: Jun. 4, 2008

(86) PCT No.: PCT/IB2008/003510
§ 371 (c)(1),
(2), (4) Date: Jan. 28, 2010

(87) PCT Pub. No.: WO2009/027850
PCT Pub. Date: Mar. 5, 2009

(65) Prior Publication Data
US 2010/0137646 A1    Jun. 3, 2010

Related U.S. Application Data

(60) Provisional application No. 60/942,337, filed on Jun. 6, 2007.

(51) Int. Cl.
*C07C 35/21* (2006.01)
*C07C 35/08* (2006.01)

(52) U.S. Cl. ........................................ 568/816; 568/834

(58) Field of Classification Search .................. 568/816, 568/834
See application file for complete search history.

(56) References Cited

U.S. PATENT DOCUMENTS

| | | | |
|---|---|---|---|
| 4,921,475 A | 5/1990 | Sibalis |
| 5,008,110 A | 4/1991 | Benecke et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Farhadieh et al. |
| 5,254,346 A | 10/1993 | Tucker et al. |
| 5,290,561 A | 3/1994 | Farhadieh et al. |
| 5,332,213 A | 7/1994 | Close |
| 5,336,168 A | 8/1994 | Sibalis |
| 5,352,456 A | 10/1994 | Fallon et al. |
| 5,382,714 A | 1/1995 | Khachik |
| 5,407,713 A | 4/1995 | Wolfong et al. |
| 6,262,284 B1 | 7/2001 | Khachik |

FOREIGN PATENT DOCUMENTS

| CN | 1659140 | 8/2005 |
|---|---|---|
| WO | WO 2004018417 | 3/2004 |

OTHER PUBLICATIONS

International Search Report PCT/IB2008/003510, 6 pgs., May 7, 2009.

*Primary Examiner* — Sikarl Witherspoon
(74) *Attorney, Agent, or Firm* — Scott D. Rothenberger; Fulbright & Jaworski

(57) ABSTRACT

The invention describes the preparation and isolation of xanthophylls from plant sources, whereby a transesterification process is utilized without the necessity of an aqueous format.

59 Claims, No Drawings

US 8,034,983 B2

PROCESS FOR THE PREPARATION OF XANTHOPHYLL CRYSTALS

CROSS-REFERENCE TO RELATED APPLICATION(S)

This application is a Section 371 National Stage Application of International No. PCT/IB2008/003510, filed 4 Jun. 2008 and published as WO 2009/027850 A2 on 5 Mar. 2009, which claims priority from the U.S. Provisional Patent Application No. 60/942,337, filed Jun. 6, 2007, the contents of which is incorporated herein in their entirety for all purposes.

FIELD OF THE INVENTION

The invention relates generally to methods isolate and purify xanthophylls such as of lutein, zeaxanthin and related compositions.

BACKGROUND OF THE INVENTION

Carotenoids are yellow, red and orange pigments that are widely distributed in nature. Although specific carotenoids have been identified in various fruits and vegetables, bird feathers, egg-yolk, poultry skin, crustaceans and macular eye region, they are especially abundant in marigold petals, corn and leafy vegetables. The correlation between dietary carotenoids and carotenoids found in human serum and plasma indicate that only selected groups of carotenoids make their way into the human blood stream to exert their effect.

Carotenoids absorb light in the 400-500 nm region of the visible spectrum. This physical characteristic imparts the yellow/red color to the pigments. Carotenoids contain a conjugated backbone composed of isoprene units, which are usually inverted at the center of the molecule, imparting symmetry. Changes in geometrical configuration about the double bonds result in the existence of many cis- and trans-isomers. Mammalian species do not synthesize carotenoids and therefore these have to be obtained from dietary sources such as fruits, vegetables and egg yolks. In the recent years, carotenoids have been attributed several health benefits, which include prevention and or protection against serious health disorders.

Carotenoids are non-polar compounds classified into two sub-classes, namely more polar compounds called xanthophylls or oxy-carotenoids and non-polar hydrocarbon carotenes like [beta]-carotene, lycopene, etc. Both the sub-classes have at least nine conjugated double bonds responsible for the characteristic color of the carotenoids. Xanthophylls have ring structures at the end of the conjugated double bond chain with polar functionalities, such as hydroxyl or keto groups. Examples of xanthophylls include lutein, zeaxanthin, capsanthin, canthaxanthin, J3-cryptoxanthin, astaxanthin, etc. As natural colorants and also for their role in human health, xanthophylls containing lutein and zeaxanthin have attracted the renewed attention of scientists and researchers in the biomedical, chemical and nutritional field in recent years.

Lutein and zeaxanthin contribute to yellow and orange-yellow color respectively. Lutein and zeaxanthin can be present in plant material in free form (non-esterified) and also as esters. Lutein is present in green leafy vegetables like spinach, kale and broccoli in the free form while fruits like mango, orange, papaya, red paprika, algae and yellow corn. These sources generally contain lutein in the form of its esters etc. Lutein is also present in the blood stream and various tissues in human body and particularly the macula, lens and retina of the eye.

Marigold (*Tagetes erecta*) flower petals are a rich source of lutein in its esterified form. The ester portion(s) are fatty acids. Dried marigold flowers contain approximately 1-1.6% carotenoids by weight and lutein esters content accounts for 90% of the total carotenoids. The xanthophyll fatty acid esters composition in marigold oleoresin chiefly consists of lutein in its ester form as di-palmitate, myristate-palmitate, palmitate-stearate, dimyristate and monoesters.

Lutein obtained by the hydrolysis of lutein esters from marigold have been found to be identical to the lutein found in fruits, vegetables and in human plasma and the macular region. After absorption, the human body cannot distinguish the source of lutein. Therefore, a widely cultivated and commercially processed raw material like marigold, which is already used by the food and feed industry, is an attractive source for lutein in view of abundant availability and cost considerations.

Essentially, lutein esters and lutein in the free form are commercially important nutraceuticals obtained from marigold flowers. Dried flowers are used for obtaining marigold extract or oleoresin. By subjecting the extract/oleoresin to saponification, xanthophylls in the free form are obtained. The resultant alkali salts of fatty acids obtained from the saponification are removed and the xanthophyll containing mixture of lutein and zeaxanthin purified further.

In the fresh marigold flowers, lutein esters exist in trans-isomeric form, whereas exposure to heat, light, oxygen, acid, etc. catalyses isomerization from trans- to cis-lutein geometric isomeric forms. As a nutraceutical and food additive, the trans-isomeric form of lutein is preferred because of better bio-availability and deeper yellow color compared to the corresponding cis-isomeric form.

In virtually all the processes described in the literature, including patents, invariably the first step of isolation and purification of the xanthophylls, such as lutein, is the aqueous saponification of oleoresin (specifically marigold) using an alcoholic and/or aqueous alkali preferably KOH. The saponification steps in these processes generally employ the use of water in the process. The processes additionally involve extracting and re extracting with solvents such as tetrahydrofuran or halogenated solvents. Additionally, many of the processes utilize elevated temperatures, such as about 70° C., that can degrade the material or isomerizes the olefinic bonds. Therefore these processes are inappropriate for industrial scale-up operations due to high cost & toxicological considerations.

Therefore, a need exists for a process to prepare solid xanthophylls that eliminates the use of water, high temperatures for saponification, and or reduced amounts of solvents.

BRIEF SUMMARY OF THE INVENTION

The present invention surprisingly provides an efficient, economical transesterification method to prepare xanthophyll materials, such as lutein and zeaxanthin. The process does not require the use of water in any of the process steps. Further, the use of organic solvents is kept to a minimum and those that are used can be removed, generally by distillation, and recycled for use in subsequent transesterification reactions. The yields of the xanthophylls produced by the processes of the invention are extremely high, generally being at least 85% of better in terms of overall yield from starting material. Additionally, the xanthophyll product prepared by the process of the invention is enriched with lutein.

In one general embodiment, the invention relates to a process for the preparation of a xanthophyll solid that includes the steps:
a) combining a xanthophyll ester containing plant oleoresin or suitable plant material with an alkali alcoholate, optionally with an aprotic organic solvent, to form a mixture;
b) adding a sufficient quantity of alcohol to the mixture until xanthophyll ester(s) cannot be detected and xanthophyll solids are formed; and
c) isolating the xanthophyll solid.

In another embodiment, the present invention pertains to a process for the preparation of a xanthophyll that includes the steps:
a) combining a xanthophyll ester containing plant oleoresin or suitable plant material with an alkali alcoholate, optionally with an aprotic organic solvent, to form a mixture;
b) heating the mixture until a liquid is produced;
c) adding a sufficient quantity of alcohol to the mixture until xanthophyll ester(s) cannot be detected;
d) cooling the reaction products of step c), thereby providing a xanthophyll solid; and
e) isolating the xanthophyll solid. In one aspect, the liquid produced in step b) is homogenous.

In still another embodiment, the components (xanthophyll ester containing plant oleoresin or suitable plant material, alkali alcoholate and an alcohol) are all combined at one time and optionally heated, optionally in the presence of a solvent.

Generally, the mode of determining when xanthophyll esters can no longer be detected is by an analytical technique used in the art, such as thin layer chromatography, gas chromatography, high performance (pressure) liquid chromatography, mass spectral analysis, etc.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Carotenoids are a class of hydrocarbons (carotenes) and the corresponding oxygenated derivatives are xanthophylls. They consist of eight isoprenoid units joined in such a manner that the arrangement of isoprenoid units is reversed at the center of the molecule so that the two central methyl groups are in a 1,6-position relationship and the remaining nonterminal methyl groups are in a 1,5-position relationship. All carotenoids may be formally derived from the acyclic $C40H_{56}$ structure (I) (Compound I), having a long central chain of conjugated double bonds, by (1) hydrogenation, (2) dehydrogenation, (3) cyclization, or (4) oxidation, or any combination of these processes. The class also includes compounds that arise from certain rearrangements or degradations of the carbon skeleton (I) (lycopene), provided that the two central methyl groups are retained.

I

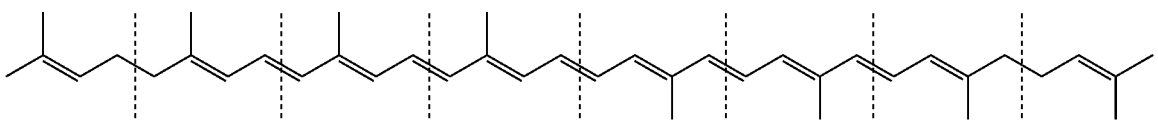

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

The present invention relates to the isolation and purification of certain oxygenated carotenoids from various plant sources as described herein.

In the specification and in the claims, the terms "including" and "comprising" are open-ended terms and should be interpreted to mean "including, but not limited to . . . ." These terms encompass the more restrictive terms "consisting essentially of" and "consisting of".

About 600 carotenoids have been isolated from natural sources. These carotenoids have been listed with their trivial and semisystematic names in Key to Carotenoids (Pfander, 1987) and in the Appendix of Carotenoids, Volume 1A (Kull & Pfander 1995) which also includes literature references for their spectroscopic and other properties. The structure is still uncertain for many of the carotenoids, including stereochemical assignments. In the cases where the structure is uncertain, resolution, followed by structural elucidation with modern spectroscopic methods (including high resolution nuclear magnetic resonance (NMR) spectroscopy) is necessary. About 370 of the naturally occurring carotenoids are chiral, bearing from one to five asymmetric carbon atoms, and in most cases one carotenoid occurs only in one configuration in Nature.

All specific names of cartenoids are based on the stem name carotene, which corresponds to the structure and numbering as in Compound II (carotene).

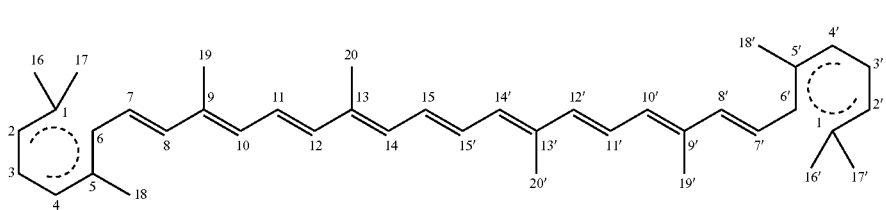

II

The name of a specific compound is constructed by adding two Greek letters as prefixes (Compound fragments III) to the stem name carotene. The Greek letter prefixes are cited in alphabetical order noted in compounds IIa.

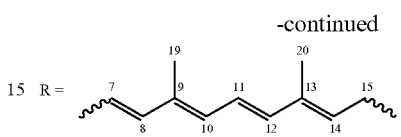

-continued

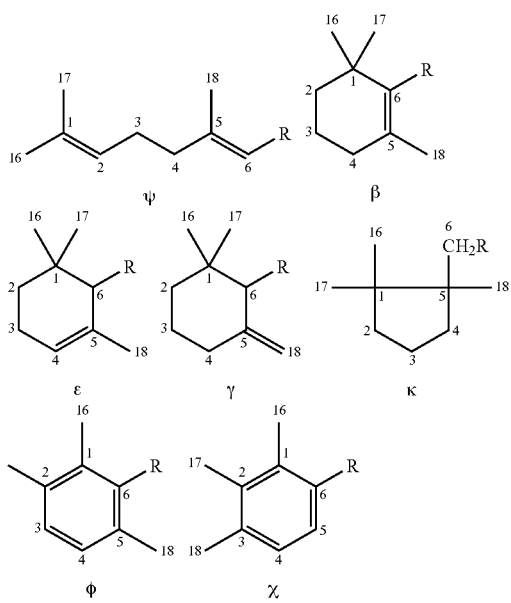

IIa

The oxygenated carotenoids (xanthophylls) most frequently include hydroxy, methoxy, carboxy, oxo, and epoxy functionality. Important and characteristic carotenoids (Compounds III through X) are lycopene (gamma, gamma-carotene) (I), beta-carotene (beta, beta-carotene) (III), alpha-carotene ((6'R)-beta, epsilon-carotene) (IV), beta-cryptoxanthin ((3R)-beta,beta-caroten-3-ol) (V), zeaxanthin ((3R,3'R)-beta, beta carotene-3,3'-diol) (VI), lutein ("xanthophyll", (3R,3'R,6'R)-beta, epsilon-carotene-3,3'-diol) (VII), neoxanthin ((3S,5R,6R,3'S,5'R,6'S)-5',6'-epoxy-6,7-didehydro-5,6,5',6'-tetrahydro-beta,beta-carotene-3,5,3'-triol) (VIII), violaxanthin ((3S,5R,6R,3'S,5'R,6'S)-5,6,5',6'-diepoxy-5,6,5',6'-tetrahydro-beta,beta-carotene-3,3'-diol) (IX), fucoxanthin ((3S,5R,6S,3'S,5'R,6'R)-5,6-epoxy-3,3',5'-trihydroxy-6',7'-didehydro-5,6,7,8,5',6'-hexahydro-beta,beta-caroten-8-one 3'-acetate) (X), canthaxanthin (beta,beta-carotene-4,4'-dione) (XI), astaxanthin ((3S,3'S)-3,3'-dihydroxy-beta,beta-carotene-4,4'-dione) (XII), beta-apo-8'-carotenal (8'-apo-beta-caroten-8'-al) (XIII) and peridinin ((3S,5R,6R,3'S,5'R,6'R)-epoxy-3,5,3'-trihydroxy-6,7-didehydro-5,6,5',6'-tetrahydro-10,11,20-trinor-beta,beta-caroten-19',11'-olide 3-acetate) (XIV).

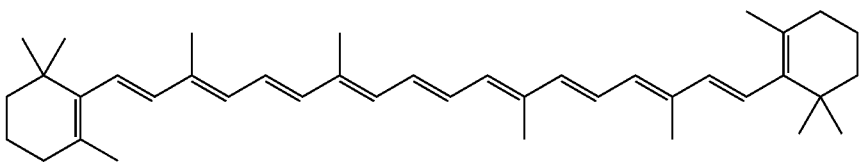

III

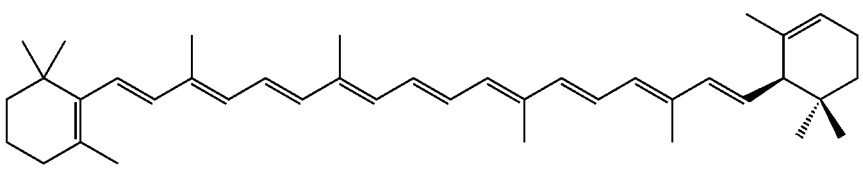

IV

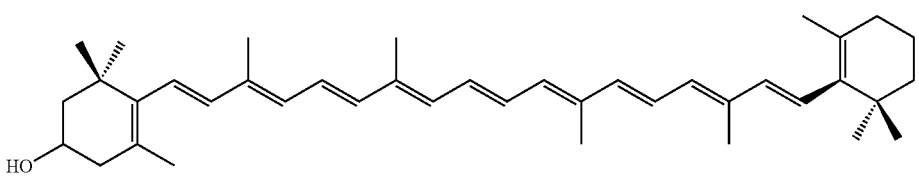

V

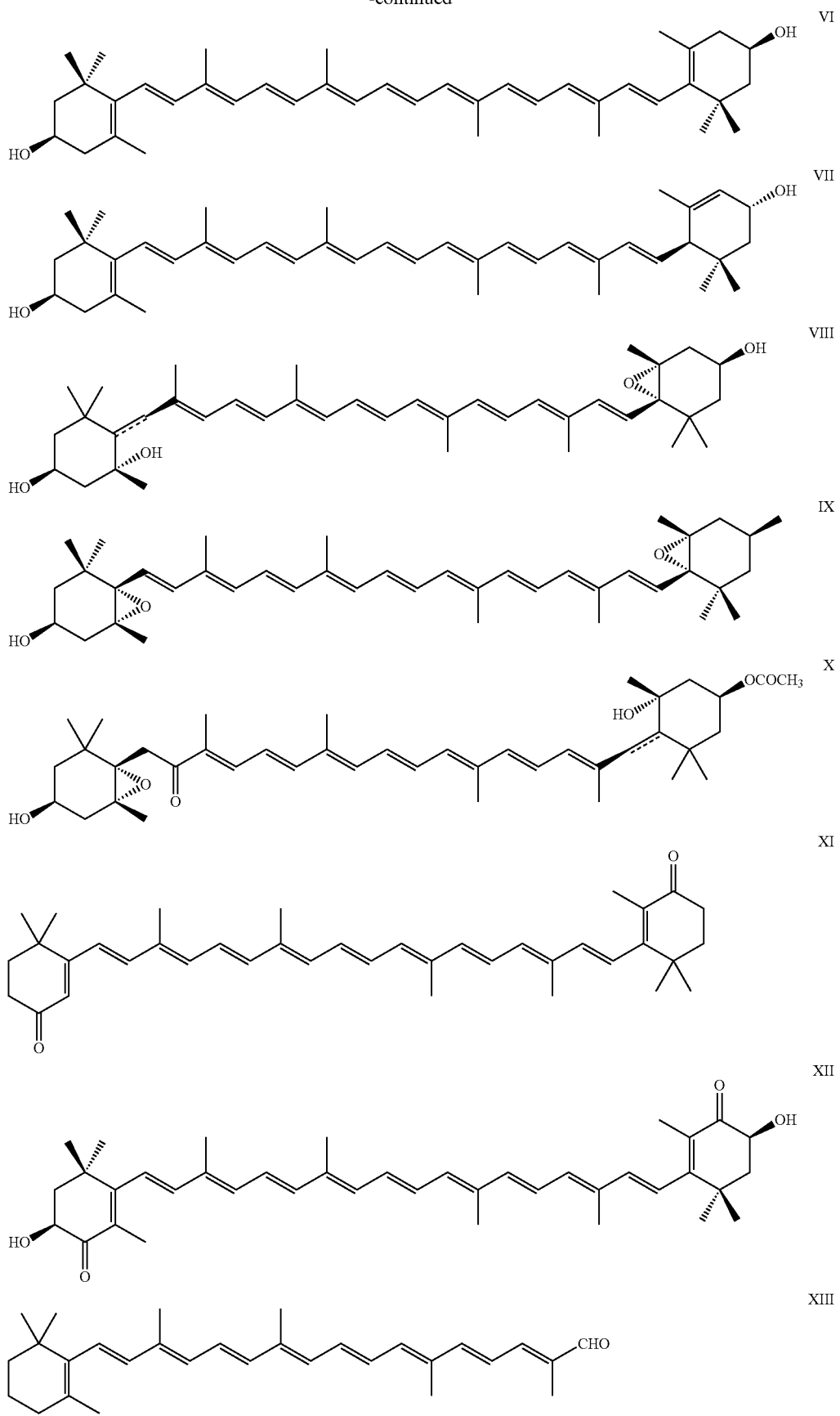

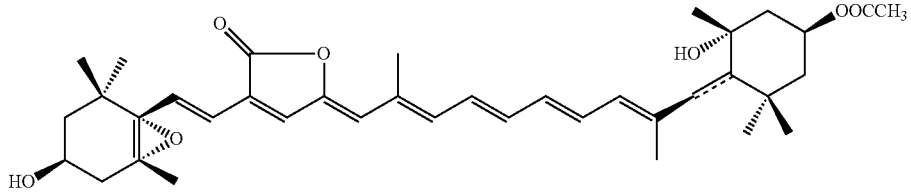

XIV

Normally carotenoids occur in Nature as the (all-E)-isomer. Some carotenoids undergo isomerization very easily during processing. For processing, it must be kept in mind that (E/Z)-isomerization can occur when a carotenoid is kept in solution. Normally the percentage of the (Z)-isomers is rather low, but it is enhanced at higher temperatures. Furthermore, the formation of (Z)-isomers is increased by exposure to light.

In commercial practice, xanthophylls of food grade quality and free of Z-lutein isomers are seldom achieved because of lack of selectivity in the raw material and improper processing conditions including high temperature drying. This results in the formation of xanthophylls of food grade quality but having higher levels of Z-lutein. The present invention avoids such increased levels of undesired Z-lutein, in part because of the relatively low temperatures used in the processes.

Humans and animals cannot synthesize xanthophylls like lutein and zeaxanthin, and the source of this has to be from diet. The occurrence of lutein and zeaxanthin in the macula has specific functions, viz., protection of the cells and tissues from ultra-violet light and reduced cataract risk. Lutein and zeaxanthin are known to comprise the macular pigment and lutein isomerizes into zeaxanthin in the macula.

There is evidence suggesting that lutein may have a protective effect against cancers of the breast, colon, lung, skin, cervix and ovaries and could bear promise in treatment of cardiovascular disease. Therefore, providing lutein to an individual for use in their diet or as nutritional supplements supports better human health and healthy vision.

Therefore, there is a high demand for xanthophyll crystals containing high amounts of trans (E)-lutein and/or zeaxanthin for its use as antioxidants, prevention of cataract and macular degeneration, as lung cancer-preventive agents, as agents for the absorption of harmful ultra-violet light from the rays of the sun and quencher of photo-induced free radical and reactive oxygen species, etc. Consequently, there is a need for providing an economical and simple process for the production of xanthophyll crystals containing high amounts of trans-lutein for using in food and nutraceutical supplements, employing toxicologically safe solvents for extraction that have GRAS [Generally Recognized As Safe] status.

The present invention relates to transesterification process for producing free xanthophylls and in particular lutein.

The process for producing xanthophyll solids, ideally as crystals, comprises the steps of:
(a) admixing a xanthophyll ester-containing plant oleoresin with an alkali alcoholate, optionally with an aprotic solvent, with stirring and heating to a temperature of about 35° C. to about 50° C. to form a liquid that is preferably homogeneous;
(b) gently adding an alcohol into the (homogenous) liquid with continuous stirring and heating under reflux conditions until no detection of xanthophyll ester is accomplished; and
(c) cooling the reaction mixture, filtering the xanthophyll solids (such as crystals), and optionally washing and then optionally drying the xanthophyll materials.

The term "xanthophyll ester" is intended to include the mono or di-esters of "free" xanthophylls and, generally, at least one fatty acid. Typically the plant source contains the xanthophyll in the esterified form as a mono- or di-C12-C18 long chain, fatty acid such as lauric, myristic, oleic, linolenic and/or palmitic acids. Lutein in marigold flowers, zeaxanthin in wolfberries and capsanthin and capsorubin in pepper plants are present as xanthophyll diesters.

The free or non-esterified xanthophyll can be found in other plants such as spinach, broccoli, kale and corn.

The term "free xanthophyll" (or free lutein, etc.) is intended to mean the carotenoid having a hydroxyl portion that remains after hydrolysis of the xanthophyll ester.

The phrase "oleoresin" is intended to be similar to xanthophyll esters. The oleoresin, however, may not necessarily be pure and can include other oils, waxes, fatty acids and the like. The xanthophyll ester-containing plant oleoresin can be extracted from the plant, preferably from the flower, fruit or root, with an appropriate organic solvent or a mixture of solvents that are themselves readily removable from the extract. The use of flowers, roots and fruits as a source of a desired xanthophyll avoids difficulty in the separation of the xanthophylls from other pigments such as chlorophyll.

The phrase "other suitable plant material" is intended to compass those materials derived from plants such as leaves, steams, stalks, roots, twigs, branches and the like that contain some amount of oleoresins as described above.

It is ideal to use oleoresins or plant materials that have a residual water content of less than about 1% by weight, ideally below about 0.5% by weight, and most ideally less than about 0.1% by weight. Increased percentages of water cause the reaction to not transesterify but to saponify the esters. It has been found to be more efficient to cause transesterification reactions to occur in terms of overall yield and purity and to decrease undesired saponification of the xanthophyll esters. Therefore, the phrase, "substantially in the absence of water" is intended to mean that the oleoresin or plant material has less than about 1% water present.

Removal of water from the oleoresin or plant material can be accomplished by various methods. Vacuum desiccation, vacuum drying, use of absorbents or adsorbents are examples. Similarly, use of non-polar solvents, such as hydrocarbons, for example hexane, to solvate the xanthophyll esters and partition from water is also possible. The solvent/xanthophyll extract can then be dried over an appropriate drying agent, such as magnesium sulfate and the like.

The phrase "alkali alcoholate" is intended to mean the alkali salts of alcohols, generally formed by the reaction of a metal, such as lithium or sodium, with an alcohol under anhydrous conditions. Suitable alkali metals that can be used include lithium, potassium, sodium, magnesium, calcium or mixtures thereof.

Suitable alcohols useful in the preparation of the alkali alcoholates include, for example, a branched or unbranched, substituted or unsubstituted C1 through C10 alcohols. Exemplary alcohols include methanol, ethanol (ethoxide), isopropanol (isopropoxide), butanol (butoxide), tertiary butanol (t-butoxide), etc. Therefore, for example, the lithium salt of the alcohols would be lithium isopropoxide, lithium butoxide, lithium ethoxide, lithium t-butoxide, etc.

The alkali alcoholate can be potassium alcoholate, sodium alcoholate, etc, preferably sodium methylate, sodium ethylate, potassium methylate, potassium ethylate or mixtures thereof.

Generally the ratio of alkali alcoholate to the oleoresin is not greater than 10% (w/w), in particular about 7% (w/w), more particularly about 5% (w/w), and more particularly about 3% (w/w).

The term "aprotic solvent" is intended to include those solvents that do not include an acidic proton, a hydroxyl proton or easily hydrolysable hydrogen atom or a solvent that does not yield or accept a proton. Suitable aprotic solvents include, for example, methylene chloride, C5 to C10 alkanes (branched and unbranched), aromatic hydrogens, etc.

In one aspect, the above process can include the addition of a non-polar solvent. The non-polar solvent can help to dissolve the oleoresin. The non-polar solvent is selected from the group of $CH_2Cl_2$, diethyl ether, petroleum ether, n-pentane, n-hexane, n-heptane, etc. The amount of the non-polar solvent should be suitable for dissolving the oleoresin.

The ratio of the non-polar solvent (aprotic solvent) to the oleoresin should be from about 1:3 to about 3:1, from about 1:2 to about 2:1, or about 1 to about 1 (weight/weight, w/w).

Generally, when the reaction is conducted at elevated temperatures, the mixture is heated and stirred for period of time sufficient to have the reactants dissolve in the reaction medium. It should be understood that all components of the reaction (the oleoresin, the alkali alcoholate and alcohol) can all be added at one time, sequentially, etc. It should also be understood that as components are added in a sequential fashion, the reaction mixture(s) can be optionally heated and optionally cooled prior to addition of a subsequent component of the reaction mixture.

The phrase "addition of a sufficient quantity of alcohol" is intended to mean that amount of an alcohol used to the alkali alcoholate/xanthophylls ester mixture that results in the disappearance of the xanthophyll ester, resulting in the free form of the xanthophyll. This amount can be determined by monitoring the reaction process progress by an analytical technique used in the art, such as thin layer chromatography, gas chromatography, high performance (pressure) liquid chromatography, mass spectral analysis, etc., using known standards of the desired product(s).

The alcohol that can be added to the reaction mixture can be a branched or unbranched, substituted or unsubstituted C1 through C10 alcohol, or mixtures thereof. Exemplary alcohols include methanol, ethanol, isopropanol, butanol, tertiary butanol, etc.

The ratio of alcohol in the step where it is added to the oleoresin or plant material is from between about 1:5 to about 5:1 (w/w), preferably from about 1:2 to about 2:1.

Generally, when the reaction is conducted at elevated temperatures, the mixture is heated and stirred for period of time sufficient to have the reactants dissolve in the reaction medium. Generally, the time to accomplish is if from between about 2 hours to about 12 hours, in particular from between about 4 hours to about 6 hours, and more particularly, from between about 1 hour to about 4 hours.

In one embodiment, upon addition of the alcohol to the reaction mixture, a homogenous solution results.

The phrase "homogenous solution" is intended to mean that the solution has a uniform appearance and composition throughout. Ideally, there should not be two or more phases present in the homogeneous solution; that is, the mixture is one phase.

The term "xanthophyll solid" is intended to mean a material that generally precipitates out of the reaction mixture in solid form. Ideally, an in one embodiment, it has been found that the present processes produce solids that are actually crystals. This helps provide highly pure xanthophyll product that requires little if any further purification.

The transesterification can be conducted at room temperature although elevated reaction temperatures are preferred. Suitable reaction temperatures for the heating the mixture containing the xanthophylls ester containing plant oleoresin or suitable plant material with the alkali alcoholate range from about 35° C. to about 100° C., more particularly from about 40° C. to about 80° C. and more particularly from about 40° C. to about 50° C. Advantageously, it is desirable to use lower reaction temperatures, such as about 40° C. to about 50° C. to prevent isomerization of the double bonds of the xanthophylls.

Likewise, upon addition of alcohol to the reaction mixture of the transesterified or partially transesterified oleoresin, the transesterification can be conducted at room temperature although elevated reaction temperatures are preferred. Suitable reaction temperatures for the heating the mixture containing the xanthophyll ester containing plant oleoresin or suitable plant material with the alkali alcoholate and alcohol range from about 35° C. to about 100° C., more particularly from about 40° C. to about 80° C. and more particularly from about 40° C. to about 50° C. Advantageously, it is desirable to use lower reaction temperatures, such as about 40° C. to about 50° C. to prevent isomerization of the double bonds of the xanthophylls.

If the process of the invention is conducted at room temperature, the xanthophyll solid may precipitate from solution. Otherwise, if the transesterification reactions were conducted at elevated temperatures, it is generally advantageous to cool the reaction temperature to about room temperature to allow the solidification process of the xanthophyll product. Ideally, the solid product results in a crystalline in form.

Generally, after the transesterifciation is complete, the lower boiling aprotic solvent(s) are removed by distillation, preferably under vacuum, or other suitable methods known in the art to remove solvent(s).

Suitable sources for the xanthophylls include marigold, Chinese wolf-berry, mango, peach, prune, acorn squash, orange, broccoli, green beans, peas, brussel sprouts, cabbage, kale, spinach, kiwi, honeydew, or mixtures thereof.

In one embodiment of the invention, commercially available dried and ground marigold flowers (*Tagetes erecta*) are used as a source of lutein.

In another embodiment, wolfberry fruits (*Lycium barbarum*) are used as a source of zeaxanthin, whereas red peppers (*Capsicum annum*) are a source of capsanthin and capsorubin.

The processes of the invention provide that the isolated xanthophyll is lutein, zeaxanthin, capsorubin, capsanthin, astaxanthin, canthaxanthin or mixtures thereof. In one aspect when marigold oleoresin is used as the starting material, the lutein is present at about 80%, zeaxanthin is present below about 20% and capsorubin, capsanthin, astaxanthin, canthaxanthin are all present below about 5%, all based on total weight of the isolated xanthophyll solids.

In another aspect, the isolated xanthophyll solids can be further treated with one or more solvents to remove any residual impurities. Typically the solvent is a protic solvent. such as an alcohol, e.g., ethanol, a hydritic hydrocarbon, e.g., a polyol, such as glycerin, or glycol, or polar solvents such as acetone, ethyl acetate, or methyl ethyl ketone.

In another aspect, the process of the invention provides that the isolated xanthophyll solids yield is at least 85%, more particularly 90% and even more particularly 95% on a weight basis based the original amount of xanthophyll in the oleoresin.

The purity of the xanthophyll content prepared by the present process is generally at least 90%, more particularly 95%, and even more particularly 99% or better, e.g., 99.5%.

In one embodiment, the present invention comprises a treatment to lower the acidity of the oleoresin before the ester-exchange (transesterification) process. By the treatment, the oleoresin should be of an acidity of below about 10 mg (milligrams) KOH/100 g (grams), preferably below about 5 mg KOH/100 g, ideally below about 4 mg KOH/100 g, more ideally below about 3 mg KOH/100 g, and most ideally below about 2 mg KOH/100 g, e.g., 1 mg KOH/100 g. The lower acidity of the oleoresin can help to obtain a high purity xanthophyll product. The pretreatment can be a recrystallization, by washing with an alkaline solution, and any other way to lower acidity.

The purified xanthophylls of the present invention can be utilized in the treatment of a diseases or conditions noted throughout this specification. They can also be used generally as nutritional supplements.

Typically the xanthophylls can be purified. For example, ultrafiltration can be used to remove unwanted components by molecular weight cut offs. The retentate from the filtration can be stored as a liquid or, for example, can then be further concentrated into a powder by spray drying, freeze drying, flash drying, fluidized bed drying, ring drying, tray drying, vacuum drying, radio frequency drying or microwave drying. Ultimately, the product should contain at least 95% by weight xanthophylls content, in particular about 99%, more particularly 99.5% or better.

The xanthophylls can be further purified by one or more methods known in the art, such as chromatography, gel chromatography, high performance liquid chromatography, crystallization, affinity chromatography, partition chromatography and the like. Identification of the particular xanthophylls can be accomplished by methods know to those skilled in the art and include $^1$H NMR, chemical degradation, chromatography and spectroscopy, especially homo- and heteronuclear two-dimensional NMR techniques for the characterization of the isolated isoprenoid compounds.

The term "purified" or "isolated" is used in reference to the purification and/or isolation of one or more xanthophylls as described above. Again using conventional methods known in the art, various xanthophylls can be separated into purified materials. In one aspect of the invention, the xanthophylls are substantially purified and isolated by techniques known in the art. The purity of the purified compounds is generally at least about 90%, preferably at least about 95%, and most preferably at least about 99% and even more preferably at least about 99.9% (e.g. about 100%) by weight.

The xanthophylls product(s) do not include residual solvent(s) as determined by analytical methods, such as gas chromatography. Therefore, the phrase "no measurable amount of residual solvent" is intended to mean that the xanthophyll isolate, when tested by an analytical method such as gas chromatography, does not show a measurable quantity of any solvent.

In certain aspects, therefore, the xanthophylls product contains less than 1 part per million, ideally less than 1 part per billion, more ideally less than 1 part per trillion of any detectable solvent. In the most ideal situation, there is no residual solvent left in the isolated xanthophyll product.

Therefore, the present invention further provides bioavailable isolated xanthophylls described herein that are useful to treat various afflictions noted herein. The xanthophylls can be administered by a number of methods, as discussed infra.

The compositions of the invention can be incorporated into various foods, drinks, snacks, etc. In one aspect, the composition can be sprinkled onto a food product, prior to consumption. If sprinkled onto a food product, a suitable carrier such as starch, sucrose or lactose, can be used to help distribute the concentration of the xanthophyll (s) making it easier to apply to the food product.

The compositions of the present invention can also be provided as supplements in various prepared food products. For the purposes of this application, prepared food product means any natural, processed, diet or non-diet food product to which a composition of the invention has been added. The compositions of the present invention can be directly incorporated into many prepared diet food products, including, but not limited to diet drinks, diet bars and prepared frozen meals. Furthermore, the compositions of the inventions can be incorporated into many prepared non-diet products, including, but not limited to candy, snack products such as chips, prepared meat products, milk, cheese, yogurt, sport bars, sport drinks, mayonnaise, salad dressing, bread and any other fat or oil containing foods. As used herein, the term "food product" refers to any substance fit for human or animal consumption.

The compositions of the invention can be added to various drinks, such as fruit juices, milkshakes, milk, etc.

The preferred method of administration is oral. The compositions of the invention can be formulated with suitable carriers such as starch, sucrose or lactose in tablets, capsules, solutions, syrups and emulsions. The tablet or capsule of the present invention can be coated with an enteric coating that dissolves at a pH of about 6.0 to 7.0. A suitable enteric coating, which dissolves in the small intestine but not in the stomach, is cellulose acetate phthalate.

Formulation of the compositions of the invention into a soft gel capsule can be accomplished by many methods known in the art. Often the formulation will include an acceptable carrier, such as an oil, or other suspending or emulsifying agent.

Suitable optional carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, wheat germ oil, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are also considered to be nutraceuticals. The term "nutraceutical" is recognized in the art and is intended to describe specific chemical compounds found in foods that can prevent disease or ameliorate an undesirable condition.

The formulations of the invention can further include various ingredients to help stabilize, or help promote the bioavailability of the components of the beneficial compositions of the invention or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals can be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Various additives can be incorporated into the present compositions. Optional additives of the present composition include, without limitation, hyaluronic acid, phospholipids, starches, sugars, fats, antioxidants, amino acids, proteins, flavorings, coloring agents, hydrolyzed starch(es) and derivatives thereof or combinations thereof.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

Compositions comprising the xanthophylls of the invention can be manufactured by methods of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the xanthophyll compositions into preparations that can be used.

The compositions of the invention can take a form suitable for virtually any mode of administration, including, for example, oral, buccal, systemic, injection, transdermal, rectal, vaginal, etc., or a form suitable for administration by inhalation or insufflation.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the xanthophyll extract compositions in aqueous or oily vehicles. The compositions can also contain formulating agents, such as suspending, stabilizing and/or dispersing agent. The formulations for injection can be presented in unit dosage form, e.g., in ampoules or in multi-dose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the xanthophyll compositions can be dried by any art-known technique, such as lyophilization, and reconstituted prior to use.

For transmucosal administration, penetrants appropriate to the barrier to be permeated are used in the formulation. Such penetrants are known in the art.

For oral administration, the compositions of the invention can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Preparations for oral administration can be suitably formulated to give controlled release of the xanthophyll composition as is well known.

For buccal administration, the compositions can take the form of tablets or lozenges formulated in conventional manner.

For rectal and vaginal routes of administration, the xanthophyll compositions can be formulated as solutions (for retention enemas) suppositories or ointments containing conventional suppository bases such as cocoa butter or other glycerides.

For nasal administration or administration by inhalation or insufflation, the xanthophyll compositions can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the xanthophyll compositions can be formulated as a depot preparation for administration by implantation or intramuscular injection. The xanthophyll compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the xanthophyll compositions for percutaneous absorption, can be used. To this end, permeation enhancers can be used to facilitate transdermal penetration of the compositions. Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other delivery systems can be employed. Liposomes and emulsions are well-known examples of delivery vehicles that can be used to deliver xanthophyll compositions. Certain organic solvents such as dimethylsulfoxide (DMSO) can also be employed, although usually at the cost of greater toxicity.

The compositions can, if desired, be presented in a pack or dispenser device, which can contain one or more unit dosage forms containing the xanthophyll compositions. The pack can, for example, comprise metal or plastic foil, such as a blister pack. The pack or dispenser device can be accompanied by instructions for administration.

Soft gel or soft gelatin capsules can be prepared, for example, without limitation, by dispersing the formulation in an appropriate vehicle (e.g., rice bran oil, and/or beeswax) to form a high viscosity mixture. This mixture is then encapsulated with a gelatin based film using technology and machinery known to those in the soft gel industry. The capsules so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally a carrier such as rice bran oil or wheat germ oil and/or beeswax if desired) and can include, apart from the xanthophylls, a hydrophilic matrix. The hydrophilic matrix, if present, is a polyethylene glycol having an average molecular weight of from about 200 to 1000. Further ingredients are optionally thickening agents and/or emulsifying agent(s). In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes is mature technologies and is all widely available to any one wishing to prepare soft gelatin capsules.

Emulsifying agents can be used to help solubilize the ingredients within the soft gelatin capsule. Specific examples of the surfactant, emulsifier, or effervescent agent include D-sorbitol, ethanol, carrageenan, carboxyvinyl polymer, carmellose sodium, guar gum, glycerol, glycerol fatty acid ester, cholesterol, white beeswax, dioctyl sodium sulfosuccinate, sucrose fatty acid ester, stearyl alcohol, stearic acid, polyoxyl 40 stearate, sorbitan sesquioleate, cetanol, gelatin, sorbitan fatty acid ester, talc, sorbitan trioleate, paraffin, potato starch, hydroxypropyl cellulose, propylene glycol, propylene glycol fatty acid ester, pectin, polyoxyethylene (105) polyoxypropylene (5) glycol, polyoxyethylene (160) polyoxypropylene (30) glycol, polyoxyethylene hydrogenated castor oil, polyoxyethylene hydrogenated castor oil 40, polyoxyethylene hydrogenated castor oil 60, polyoxyl 35 castor oil, polysorbate 20, polysorbate 60, polysorbate 80, macrogol 400, octyldodecyl myristate, methyl cellulose, sorbitan monooleate, glycerol monostearate, sorbitan monopalmitate, sorbitan monolaurate, lauryl dimethylamine oxide solution, sodium lauryl sulfate, lauromacrogol, dry sodium carbonate, tartaric acid, sodium hydroxide, purified soybean lecithin, soybean lecithin, potassium carbonate, sodium hydrogen carbonate, medium-chain triglyceride, citric anhydride, cotton seed oil-soybean oil mixture, and liquid paraffin.

The present invention also provides packaged formulations of the compositions of the invention and instructions for use of the product for appropriate condition(s). Typically, the packaged formulation, in whatever form, is administered to an individual in need thereof. Typically, the dosage requirement is between about 1 to about 4 dosages a day.

Although the present invention describes the preparation, use, manufacture and packaging of the compositions of the invention in soft gelatin capsules for treatment of various conditions, it should not be considered limited to only soft gelatin capsules. Ingestible compositions of the invention can be delivered in traditional tablets, pills, lozenges, elixirs, emulsions, hard capsules, liquids, suspensions, etc. as described above.

The xanthophyll compositions of the invention, or compositions thereof, will generally be used in an amount effective to achieve the intended result, for example in an amount effective to treat or prevent the particular related condition being treated. The composition can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a composition of the invention to a patient suffering from pain provides therapeutic benefit not only when the underlying condition is eradicated or ameliorated, but also when the patient reports a decrease in the severity or duration of the physical discomfort associated with the pain.

For prophylactic administration, the composition can be administered to a patient at risk of developing one of the previously described conditions.

The amount of composition administered will depend upon a variety of factors, including, for example, the particular indication being treated, the mode of administration, whether the desired benefit is prophylactic or therapeutic, the severity of the indication being treated and the age and weight of the patient, etc. Determination of an effective dosage is well within the capabilities of those skilled in the art.

Total dosage amounts of a xanthophyll composition will typically be in the range of from about 0.0001 or 0.001 or 0.01 mg/kg/day to about 100 mg/kg/day, but may be higher or lower, depending upon, among other factors, the activity of the components, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. Skilled artisans will be able to optimize effective local dosages without undue experimentation.

The following paragraphs enumerated consecutively from 1 through 59 provide for various aspects of the present invention. In one embodiment, in a first paragraph (1), the present invention provides a process for the preparation of a xanthophyll solid including the steps:

a) combining a xanthophyll ester containing plant oleoresin or suitable plant material with an alkali alcoholate, optionally with an aprotic organic solvent, to form a mixture;

b) adding a sufficient quantity of alcohol to the mixture until xanthophyll ester(s) cannot be detected and xanthophyll solids are formed; and c) isolating the xanthophyll solid.

2. The process of paragraph 1, wherein the suitable plant material is a xanthophyll ester containing plant oleoresin.

3. The process of either of paragraphs 1 or 2, wherein the alkali metal of the alkali alcoholate is lithium, potassium, sodium, magnesium, calcium or mixtures thereof.

4. The process of any of paragraphs 1 through 3, wherein the alcohol of the alcoholate is a branched or unbranched, substituted or unsubstituted C1 through a C10 alcohol.

5. The process of any of paragraphs 1 through 4, wherein the optional aprotic organic solvent is methylene chloride, C5 to C10 alkanes, aromatic hydrocarbons, or an alkyl acetate.

6. The process of any of paragraphs 1 through 5, wherein the alcohol added to the mixture is a branched or unbranched, substituted or unsubstituted C1 through a C10 alcohol.

7. The process of any of paragraphs 1 through 6, wherein the mode of detection is by is by an analytical technique used in the art, such as thin layer chromatography, gas chromatography, high performance (pressure) liquid chromatography, mass spectral analysis, etc.

8. The process of any of paragraphs 1 through 7, wherein the mixture of step a) is heated to a temperature range of about 35° C. to about 100° C.

9. The process of paragraph 8, wherein the temperature range is from about 40° C. to about 50° C.

10. The process of any of paragraph 1 through 9, wherein the mixture is combined for a sufficient period of time to afford a homogeneous liquid.

11. The process of paragraph 10, wherein the mixture of step b) is heated to a temperature range of about 35° C. to about 100° C.

12. The process of paragraph 11, wherein the temperature range is from about 40° C. to about 50° C.

13. The process of any of paragraphs 1 through 12, wherein the mixture of step b) is heated to a temperature range of about 35° C. to about 100° C.

14. The process of paragraph 13, wherein the temperature range is from about 40° C. to about 50° C.

15. The process of either of paragraphs 13 or 14, wherein the mixture of step b) is cooled to at least ambient temperature.

16. The process of any of paragraphs 1 through 15, wherein the xanthophyll ester containing plant oleoresin or suitable plant material is from marigold, Chinese wolf-berry, mango, peach, prune, acorn squash, orange, broccoli, green beans, peas, brussels sprouts, cabbage, kale, spinach, kiwi, honeydew, or mixtures thereof.

17. The process of any of paragraphs 1 through 16, wherein the isolated xanthophyll is lutein, zeaxanthin, capsorubin, capsanthin, astaxanthin, canthaxanthin or mixtures thereof.

18. The process of paragraph 17, wherein lutein is present at about 80%, zeaxanthin is present below about 20% and capsorubin, capsanthin, astaxanthin, canthaxanthin are all present below about 5%, all based on the original weight of plant oleoresin or suitable plant material.

19. The process of any of paragraphs 1 through 18, wherein the isolated xanthophyll solids are crystalline.

20. The process of any of paragraphs 1 through 19, wherein the xanthophyll solid is treated with a protic solvent.

21. The process of paragraph 20, wherein the protic solvent is an alcohol.

22. The process of any of paragraphs 1 through 21, wherein the isolated xanthophyll solids yield is at least 85% on a weight basis.

23. The process of paragraph 22, wherein the xanthophyll solids yield is at least 90% on a weight basis.

24. The process of paragraph 23, wherein the xanthophyll solids yield is at least 95% on a weight basis.

25. A process for the preparation of a xanthophyll solid comprising the steps:

a) combining a xanthophyll ester containing plant oleoresin or suitable plant material with an alkali alcoholate, optionally with an aprotic organic solvent, to form a mixture;

b) heating the mixture until a homogeneous liquid is produced;

c) adding a sufficient quantity of alcohol to the mixture until xanthophyll ester(s) cannot be detected;

d) cooling the reaction products of step c), thereby providing a xanthophyll solid; and e) isolating the xanthophyll solid.

26. The process of paragraph 25, wherein the suitable plant material is a xanthophyll ester containing plant oleoresin.

27. The process of either of paragraphs 25 or 26, wherein the alkali metal of the alkali alcoholate is lithium, potassium, sodium, magnesium, calcium or mixtures thereof.

28. The process of any of paragraphs 25 through 27, wherein the alcohol of the alcoholate is a branched or unbranched, substituted or unsubstituted C1 through a C10 alcohol.

29. The process of any of paragraphs 25 through 28, wherein the optional aprotic organic solvent is methylene chloride, C5 to C10 alkanes, aromatic hydrocarbons, or an alkyl acetate.

30. The process of any of paragraphs 25 through 29, wherein the temperature range of step b) is from about 35° C. to about 100° C.

31. The process of paragraph 30, wherein the temperature range is from about 40° C. to about 50° C.

32. The process of any of paragraphs 25 through 31, wherein the alcohol added to the mixture in step c) is a branched or unbranched, substituted or unsubstituted C1 through a C10 alcohol.

33. The process of any of paragraphs 25 through 32, wherein the temperature range of step c) is from about 35° C. to about 100° C.

34. The process of paragraph 33, wherein the temperature range is from about 40° C. to about 50° C.

35. The process of any of paragraphs 25 through 34, wherein the mode of detection is by an analytical technique used in the art, such as thin layer chromatography, gas chromatography, high performance (pressure) liquid chromatography, mass spectral analysis, etc.

36. The process of any of paragraphs 25 through 35, wherein the xanthophyll ester containing plant oleoresin or suitable plant material is from marigold, Chinese wolf-berry, mango, peach, prune, acorn squash, orange, broccoli, green beans, peas, brussels sprouts, cabbage, kale, spinach, kiwi, honeydew, or mixtures thereof.

37. The process of any of paragraphs 25 through 36, wherein the isolated xanthophyll is lutein, zeaxanthin, capsorubin, capsanthin, astaxanthin, canthaxanthin or mixtures thereof.

38. The process of paragraph 37, wherein lutein is present at about 80%, zeaxanthin is present below about 20% and capsorubin, capsanthin, astaxanthin, canthaxanthin are all present below about 5%, all based on the original weight of plant oleoresin or suitable plant material.

39. The process of any of paragraphs 25 through 38, wherein the isolated xanthophyll solids are crystalline.

40. The process of any of paragraphs 25 through 39, wherein the xanthophyll solid is treated with a protic solvent.

41. The process of paragraph 40, wherein the protic solvent is an alcohol.

42. The process of any of paragraphs 25 through 41, wherein the isolated xanthophyll solids yield is at least 85% on a weight basis.

43. The process of paragraph 42, wherein the xanthophyll solids yield is at least 90% on a weight basis.

44. The process of paragraph 43, wherein the xanthophyll solids yield is at least 95% on a weight basis.

45. A process for the preparation of a xanthophyll solid comprising the steps:
    combining a xanthophyll ester containing plant oleoresin or suitable plant material with an alkali alcoholate, optionally with an aprotic organic solvent and a sufficient quantity of alcohol to provide a mixture, such that the final reaction produces a product wherein xanthophyll ester(s) cannot be detected and xanthophyll solids are formed; and
    isolating the xanthophyll solid.

46. The process of paragraph 45, wherein the mixture is heated.

47. The process of any of paragraphs 1 through 46, wherein the xanthophylls solid has no measurable amount of residual solvent.

48. The process of any of paragraphs 1 through 46, wherein the oleoresin or suitable plant material has less than about 1% by weight of water.

49. The process of any of paragraphs 1 through 48, wherein acidity of the oleoresin or suitable plant material is less than about 10 mg KOH/100 g.

50. The process of paragraph 49, wherein the acidity is below about 4 mg KOH/100 g.

51. The process of any of paragraphs 1 through 50, wherein the alkali alcoholate to the oleoresin or plant material is not greater than 10% (w/w).

52. The process of paragraph 51, wherein the ratio is not greater than about 7% (w/w).

53. The process of paragraph 52, wherein the ratio is not greater than about 5% (w/w).

54. The process of paragraph 53, wherein the ratio of not greater than about 3% (w/w).

55. The process of any of paragraphs 1 through 54, wherein the ratio of aprotic solvent to the oleoresin or plant material should be from about 1:3 to about 3:1 by weight.

56. The process of paragraph 55, wherein the ratio is from about 1:2 to about 2:1 by weight.

57. The process of paragraph 56, wherein the ratio is from about 1 to about 1 by weight.

58. The process of any of paragraphs 1 through 57, wherein the ratio of alcohol to the oleoresin or plant material is from between about 1:5 to about 5:1 (w/w).

59. The process of paragraph 58, wherein the ratio is between about 1:2 to about 2:1 (w/w).

The following examples are not to be meant as limiting but are presented to provide additional information and support for the invention.

EXAMPLES

Example 1

12 g marigold oleoresin containing 47.8% xanthophyll content was placed into a 250 mL flask with 0.3 g sodium methylate (30%, Sodium Methylate in 1 g methanol) and 40 mL $CH_2Cl_2$. The mixture was stirred and heated until dissolution at about 40° C., at which time 60 mL of methanol was added to the flask with continuous stirring over about 10 minutes followed by refluxing the mixture with stirring for about 6 hours until the disappearance of xanthophyll ester was observed by thin layer chromatography. The residual $CH_2Cl_2$ was removed by distillation, the mixture was cooled down and filtered to provide xanthophyll crystals. The crystals were collected and washed with ethanol. The resulting crystals were dried at ambient temperature to afford 6.3 g xanthophyll crystals (99.1 percent based on original xanthophylls content). Xanthophyll content was 90.2% by weight as determined by UV. No solvent was detected by gas chromatography.

Example 2

20 g marigold oleoresin containing 45.9% xanthophyll content was placed in a 250 mL flask with 30 g methanol 60 g isopropanol and 15 g $CH_2Cl_2$. The mixture was stirred and heated at about 50° C. and then 0.3 g sodium methylate (30%, Sodium Methylate in 1 g methanol) was added into the flask with continuous stirring. The reaction mixture was heated at reflux for about 2 hrs, until the disappearance of xanthophyll ester by observed by thin layer chromatography. The mixture was cooled down and filtered to collect xanthophyll crystals. The crystals were washed with 20 g ethanol. The resulting crystals were vacuum dried and 9.0 g xanthophyll crystals were obtained. (90% based on original xanthophylls content.) Xanthophyll content was 91.8% by weight as determined by UV. No solvent was detected by gas chromatography.

Example 3

6 g marigold oleoresin containing 45.9% xanthophyll content was placed into a 100 mL flask along 0.15 g sodium methylate (30%, Sodium Methylate in 0.5 g methanol) and 20 mL $CH_2Cl_2$. The mixture was stirred and heated until dissolution occurred at about 40° C. 30 mL ethanol was added to the flask with stirring over a period of about 10 minutes, followed by refluxing with stirring for about 4 hrs, until the disappearance of xanthophyll ester(s) by thin layer chromatography. The residual $CH_2Cl_2$ was removed by distillation, the mixture was cooled down and filtered to afford xanthophyll crystals. The crystals were washed with 20 mL ethanol. The resulting crystals were dried at ambient temperature and 3.0 g xanthophyll crystals were obtained. Xanthophyll content was 85.1% by weight as determined by UV. The yield was 92.7%. No solvent was detected by gas chromatography.

Example 4

Recrystallization 6 g commercial grade marigold oleoresin containing 12.1% xanthophyll content was mixed with 10 mL of n-hexanes and stirred until the mixture became a homogenous suspension. The suspension was allowed to settle for 10 minutes. The upper phase was then decanted and the resulting precipitate (solid) was washed with 5 mL n-hexane. The precipitate had an acidity of 6.9 mg KOH/100 g. Water content of 0.1% by weight.

The washed precipitate was placed into a 100 mL flask along with 0.15 g sodium methylate (30%, Sodium Methylate in 0.5 g methanol) and 20 mL $CH_2Cl_2$. The mixture was stirred and heated until dissolution occurred at about 40° C. 40 mL ethanol were added to the flask with continuous stirring over a period of 10 minutes followed by heating at reflux with stirring for about 2 hours until the disappearance of xanthophyll ester(s) by thin layer chromatography. The residual $CH_2Cl_2$ was removed by distillation, the mixture was cooled and filtered to afford xanthophyll crystals. The crystals were washed with 20 mL ethanol. The resulting crystals were dried at ambient temperature and 0.76 g xanthophyll crystals were obtained. Xanthophyll content was 95.1% by weight as determined by UV. The yield is 99.5%. No solvent was detected by gas chromatography.

Example 5

First wash with $Na_2CO_3$ 20 g commercial grade marigold oleoresin containing 12.1% xanthophyll content was placed in a reactor provided with agitation and heated to 40° C. Under a slow agitation, 20 g of 1% $Na_2CO_3$ (1% by weight of $Na_2CO_3$, aqueous solution) were added to the reactor and the mixture was stirred for 5 minutes. Two phases immediately separated by centrifugation. The water phase was discarded and the oleoresin was vacuum dried and had an acidity of 4.5 mg KOH/100 g and a water content of 0.5% (w/w).

The dried oleoresin was placed in a 250 mL flask to which was added 1.2 g sodium methylate (30%, Sodium Methylate in 4 g methanol) and 20 mL $CH_2Cl_2$. The mixture was stirred and heated until dissolution occurred at about 45° C. 100 mL methanol was added to the flask with continuous stirring over a period of about 10 minutes followed by refluxing with stirring for about 12 hours. The residual $CH_2Cl_2$ was removed by distillation, the mixture was cooled and 2.38 g of xanthophyll crystals were obtained. Xanthophyll content was 93.1% by weight as determined by UV in the resulting paste and the yield is 91.6%. No solvent was detected by gas chromatography.

Example 6

Zeaxanthin from Wolfberrires [*Lyceum barbarum*]

10 g wolfberry oleoresin (the acidity was 4.5 mg KOH/100 g) containing 23.1% xanthophyll content was taken into a 250 mL flask, with 50 g ethanol and 0.5 g potassium ethoxide (97%, solid). The mixture was stirred and heated at about 45° C. with continuous stirring for about 4 hours until no detection of xanthophyll ester by thin layer chromatography was observed.

The mixture was cooled down and filtrated. A precipitate of xanthophyll crystals was obtained which were was washed with 10 g ethanol. The resulting crystals were vacuum dried to afford 2.2 g xanthophyll crystals. Xanthophyll content was 95.7% by weight as determined by UV. The yield was 91.3%.

Example 7

Zeaxanthin from wolfberrires [*Lyceum barbarum*]

10 g wolfberry oleoresin (the acidity was 4.5 mg KOH/100 g) containing 23.1% xanthophyll content was taken into a 250 mL flask with 50 g isopropanol. The mixture was heated and stirred to 50° C. to which was then added 0.5 g lithium butoxide (20%, lithium butoxide in cyclohexane of 2.5 g). The mixture was stirred for 3.5 hours until no detection of xanthophylls ester was noted by thin layer chromatography.

The mixture was cooled and a precipitate of xanthophyll crystals was filtered. The crystals were washed with 10 g ethanol. The resulting crystals were vacuum dried to afford 1.6 g xanthophyll crystals. Xanthophyll content was 98.2% by weight as determined by UV. The yield was 85.0%.

Example 8

Zeaxanthin from Wolfberrires [*Lyceum barbarum*]

10 g wolfberry oleoresin (the acidity was 4.5 mg KOH/100 g) containing 23.1% xanthophyll content was taken into a 250 mL flask along with 50 g isopropanol. The mixture was heated and stirred a 50° C. to which was then added 0.5 g lithium butoxide (20%, lithium butoxide in cyclohexane of 2.5 g). The resulting mixture was heated and stirred at 50° C. for 3.5 our until xanthophyll ester was not detected by thin layer chromatography.

The mixture was cooled and a precipitate of xanthophyll crystals was filtered. The crystals were washed with 10 g ethanol. The resulting crystals were vacuum dried and 1.6 g xanthophyll crystals were obtained. Xanthophyll content was 98.2% by weight as determined by UV. The yield was 85.0%.

Gas Chromatography Conditions

Detection of solvent remaining in examples 1 through 8. Instrument and reagents:

| | |
|---|---|
| Gas chromatograph: | Agilent 6890N |
| Workstation: | GC Chemstation Rev.A.10.02; |
| Headspace type: | Agilent Headspace Sample 7694E; |
| Column: | Agilent HP-INNOWAX 30 m × 0.320 mm × 0.25 micron | methylene chloride (Chromatographic Pure)☐
Water
lutein ester (examples 1-5)
Palmitic acid (Sigma P0500)

Preparation and Detection
comparative sample 150 mg of Palmitic acid plus 0.7 μl (microliters) of methylene chloride
Samples: 150 mg of the resulting crystals of examples 1-5.
Results

|  |  | Peak area | Resulting content |
|---|---|---|---|
| Comparative sample |  | 2084.0/2083.6 | 0.01% |
| sample | Example 1 | No peak | 0 |
|  | Example 2 | No peak | 0 |
|  | Example 3 | No peak | 0 |
|  | Example 4 | No peak | 0 |
|  | Example 5 | No peak | 0 |

UV Test Procedure

For Examples 1 through 8

Chemicals: THF-Tetrahydrofuran
Ethanol or reagent alcohol
Apparatus: Volumetric flasks 50 ml, Pipettes, Funnels, Quartz cuvettes UV spectrophotometer
Procedure:
1. The optimum sample quantity was 10-20 mg. Raw material or fill blend was weighed accurately in a 50 ml volumetric flask and recorded as W.
2. The sample was dissolved in 25 ml of THF. The volumetric flask was filled to volume with ethanol.
3. A 1 ml sample of the THF-ethanol solution was sampled and diluted with 50 ml with ethanol volumetrically or an appropriate dilution for the absorbance to read in the 0.5 AU range.
4. The sample was mixed and a quartz cell for UV measurement was utilized. Ethanol was used as a blank.
5. Further dilution of 1:10 could be required. The dilution factor was recorded.
6. The optimal wavelength was 446 nm. The absorption A was recorded at this wavelength.
Calculation:

Quantity of 20% lutein in mg=(dilution factor×$A_{446}$)/ 255 ml/mg.    1.

255 ml/mg is the extinction coefficient.

% of concentration=(quantity of lutein)/$W$×100%    2.

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A non-aqueous process for the preparation of a non-esterified xanthophyll solid comprising the steps:
a) combining a xanthophyll ester containing plant oleoresin or suitable plant material with an alkali alcoholate, optionally with an aprotic organic solvent, to form a mixture;
b) adding a sufficient quantity of alcohol to the mixture until xanthophyll ester(s) cannot be detected and non-esterified xanthophyll solids are formed;
c) adding a sufficient amount of alcohol to the non-esterified xanthophyll solids of step b) at ambient temperature to cause precipitation of the non-esterified xanthophyll solids; and
d) isolating the non-esterified xanthophyll solids of step c), wherein water is substantially absent from any step.

2. The process of claim 1, wherein the suitable plant material is a xanthophyll ester containing plant oleoresin.

3. The process of claim 1, wherein the alkali metal of the alkali alcoholate is lithium, potassium, sodium, magnesium, calcium or mixtures thereof.

4. The process of claim 1, wherein the alcohol of the alcoholate is a branched or unbranched, substituted or unsubstituted C1 through a C10 alcohol.

5. The process of claim 1, wherein the optional aprotic organic solvent is methylene chloride, a C5 to C10 alkane, an aromatic hydrocarbons, or an alkyl acetate.

6. The process of claim 1, wherein the alcohol added to the mixture is a branched or unbranched, substituted or unsubstituted C1 through a C10 alcohol.

7. The process claim 1, wherein the mode of detection is by thin layer chromatography, gas chromatography, high performance (pressure) liquid chromatography or mass spectral analysis.

8. The process of claim 1, wherein the mixture of step a) is heated to a temperature range of about 35° C. to about 100° C.

9. The process of claim 8, wherein the temperature range is from about 40° C. to about 50° C.

10. The process of claim 1, wherein the mixture is combined for a sufficient period of time to afford a homogeneous liquid.

11. The process of claim 10, wherein the mixture of step b) is heated to a temperature range of about 35° C. to about 100° C.

12. The process of claim 11, wherein the temperature range is from about 40° C. to about 50° C.

13. The process of claim 1, wherein the mixture of step b) is heated to a temperature range of about 35° C. to about 100° C.

14. The process of claim 13, wherein the temperature range is from about 40° C. to about 50° C.

15. The process of claim 13, wherein the mixture of step b) is cooled to at least ambient temperature.

16. The process of claim 1, wherein the xanthophyll ester containing plant oleoresin or suitable plant material is from marigold, Chinese wolf-berry, mango, peach, prune, acorn squash, orange, broccoli, green beans, peas, brussels sprouts, cabbage, kale, spinach, kiwi, honeydew, or mixtures thereof.

17. The process of claim 1, wherein the isolated non-esterified xanthophyll solid is lutein, zeaxanthin, capsorubin, capsanthin, astaxanthin, canthaxanthin or mixtures thereof.

18. The process of claim 17, wherein lutein is present at about 80%, zeaxanthin is present below about 20% and capsorubin, capsanthin, astaxanthin, canthaxanthin are all present below about 5%, all based on the original weight of plant oleoresin or suitable plant material.

19. The process of claim 1, wherein the isolated non-esterified xanthophyll solids are crystalline.

20. The process of claim 1, wherein the isolated non-esterified xanthophyll solid is treated with a protic solvent.

21. The process of claim 20, wherein the protic solvent is an alcohol.

22. The process of claim 1, wherein the isolated non-esterified xanthophyll solids yield is at least 85% on a weight basis.

23. The process of claim 22, wherein the xanthophyll solids yield is at least 90% on a weight basis.

24. The process of claim 23, wherein the xanthophyll solids yield is at least 95% on a weight basis.

25. A non-aqueous process for the preparation of a non-esterified xanthophyll solid comprising the steps:

a) combining a xanthophyll ester containing plant oleoresin or suitable plant material with an alkali alcoholate, optionally with an aprotic organic solvent, to form a mixture;

b) heating the mixture until a homogeneous liquid is produced;

c) adding a sufficient quantity of alcohol to the mixture until xanthophyll ester(s) cannot be detected;

d) cooling the reaction products of step c), thereby providing a non-esterified xanthophyll solid; and e) isolating the non-esterified xanthophyll solid, wherein water is substantially absent from any step.

26. The process of claim 25, wherein the suitable plant material is a xanthophyll ester containing plant oleoresin.

27. The process of claim 25, wherein the alkali metal of the alkali alcoholate is lithium, potassium, sodium, magnesium, calcium or mixtures thereof.

28. The process of claim 25, wherein the alcohol of the alcoholate is a branched or unbranched, substituted or unsubstituted C1 through a C10 alcohol.

29. The process of claim 25, wherein the optional aprotic organic solvent is methylene chloride, a C5 to C10 alkane, an aromatic hydrocarbons, or an alkyl acetate.

30. The process of claim 25, wherein the temperature range of step b) is from about 35° C. to about 100° C.

31. The process of claim 30, wherein the temperature range is from about 40° C. to about 50° C.

32. The process of claim 25, wherein the alcohol added to the mixture in step c) is a branched or unbranched, substituted or unsubstituted C1 through a C10 alcohol.

33. The process of claim 25, wherein the temperature range of step c) is from about 35° C. to about 100° C.

34. The process of claim 33, wherein the temperature range is from about 40° C. to about 50° C.

35. The process of claim 25, wherein the mode of detection is by thin layer chromatography, gas chromatography, high performance (pressure) liquid chromatography or mass spectral analysis.

36. The process of claim 25, wherein the xanthophyll ester containing plant oleoresin or suitable plant material is from marigold, Chinese wolf-berry, mango, peach, prune, acorn squash, orange, broccoli, green beans, peas, brussels sprouts, cabbage, kale, spinach, kiwi, honeydew, or mixtures thereof.

37. The process of claim 25, wherein the isolated non-esterified xanthophyll solid is lutein, zeaxanthin, capsorubin, capsanthin, astaxanthin, canthaxanthin or mixtures thereof.

38. The process of claim 37, wherein lutein is present at about 80%, zeaxanthin is present below about 20% and capsorubin, capsanthin, astaxanthin, canthaxanthin are all present below about 5%, all based on the original weight of plant oleoresin or suitable plant material.

39. The process of claim 25, wherein the isolated non-esterified xanthophyll solids are crystalline.

40. The process of claim 25, wherein the isolated non-esterified xanthophyll solid is treated with a protic solvent.

41. The process of claim 40, wherein the protic solvent is an alcohol.

42. The process of claim 25, wherein the isolated non-esterified xanthophyll solids yield is at least 85% on a weight basis.

43. The process of claim 42, wherein the xanthophyll solids yield is at least 90% on a weight basis.

44. The process of claim 43, wherein the xanthophyll solids yield is at least 95% on a weight basis.

45. A non-aqueous process for the preparation of a non-esterified xanthophyll solid comprising the steps:

combining a xanthophyll ester containing plant oleoresin or suitable plant material with an alkali alcoholate, optionally with an aprotic organic solvent and a sufficient quantity of alcohol to provide a mixture, such that the final reaction produces a product wherein xanthophyll ester(s) cannot be detected and non-esterified xanthophyll solids are formed;

adding a sufficient amount of alcohol to the non-esterified xanthophyll at ambient temperature to cause precipitation of a non-esterified xanthophyll; and isolating the non-esterified xanthophyll-solid, wherein water is substantially absent from any step.

46. The process of claim 45, wherein the mixture is heated.

47. The process of claim 45, wherein the isolated non-esterified xanthophyll has no measurable amount of residual solvent.

48. The process of claim 45, wherein the oleoresin or suitable plant material has less than about 1% by weight of water.

49. The process of claim 45, wherein acidity of the oleoresin or suitable plant material is less than about 10 mg KOH/100 g.

50. The process of claim 49, wherein the acidity is below about 4 mg KOH/100 g.

51. The process of claim 45, wherein the alkali alcoholate to the oleoresin or plant material is not greater than 10% (w/w).

52. The process of claim 51, wherein the ratio is not greater than about 7% (w/w).

53. The process of claim 52, wherein the ratio is not greater than about 5% (w/w).

54. The process of claim 53, wherein the ratio of not greater than about 3% (w/w).

55. The process of claim 45, wherein the ratio of aprotic solvent to the oleoresin or plant material should be from about 1:3 to about 3:1 by weight.

56. The process of claim 55, wherein the ratio is from about 1:2 to about 2:1 by weight.

57. The process of claim 56, wherein the ratio is from about 1 to about 1 by weight.

58. The process of claim 45, wherein the ratio of alcohol to the oleoresin or plant material is from between about 1:5 to about 5:1 (w/w).

59. The process of claim 58, wherein the ratio is between about 1:2 to about 2:1 (w/w).

* * * * *